United States Patent
Suzuki

(10) Patent No.: US 9,945,803 B2
(45) Date of Patent: Apr. 17, 2018

(54) GAS DETECTING DEVICE AND METHOD THEREOF

(71) Applicant: FUJI ELECTRIC CO., LTD., Kawasaki (JP)

(72) Inventor: Takuya Suzuki, Hachioji (JP)

(73) Assignee: FUJI ELECTRIC CO., LTD., Tokyo (JP)

(*) Notice: Subject to any disclaimer, the term of this patent is extended or adjusted under 35 U.S.C. 154(b) by 222 days.

(21) Appl. No.: 14/959,634

(22) Filed: Dec. 4, 2015

(65) Prior Publication Data

US 2016/0084786 A1 Mar. 24, 2016

Related U.S. Application Data

(63) Continuation of application No. PCT/JP2014/082659, filed on Dec. 10, 2014.

(30) Foreign Application Priority Data

Dec. 13, 2013 (JP) .................................. 2013-257735

(51) Int. Cl.
  *G01N 27/12* (2006.01)
  *G01N 27/16* (2006.01)

(52) U.S. Cl.
  CPC ............. *G01N 27/12* (2013.01); *G01N 27/16* (2013.01)

(58) Field of Classification Search
  CPC .............................. G01N 27/12; G01N 27/16
  See application file for complete search history.

(56) References Cited

U.S. PATENT DOCUMENTS

2016/0103082 A1* 4/2016 Kimura ................. G01N 25/20
73/25.01

FOREIGN PATENT DOCUMENTS

| JP | 2001-318069 | 11/2001 |
| JP | 2002-98665 | 4/2002 |
| JP | 2005-17182 | 1/2005 |
| JP | 2007-24508 | 2/2007 |
| JP | 2007-271636 | 10/2007 |
| JP | 4347641 | 10/2009 |

(Continued)

OTHER PUBLICATIONS

English Machine Translation of Mitsuo et al., JP 2007-024508 A, Feb. 1, 2007, Translated Aug. 2017.*

(Continued)

*Primary Examiner* — Hezron E Williams
*Assistant Examiner* — David Z Huang

(57) ABSTRACT

A gas detecting method includes heating a gas detector, formed of a gas sensing layer and an adsorption layer, for an oxygen adsorption period $t_0$ at an oxygen adsorption temperature $T_0$; heating the gas detector for a target gas adsorption period $t_1$ at a target gas adsorption temperature $T_1$ at which a target gas is adsorbed to the adsorption layer, heating the gas detector for a target gas desorption period $t_2$ at a target gas desorption temperature $T_2$ at which the target gas adsorbed to the adsorption layer is desorbed to move to the gas sensing layer; and calculating a gas concentration of the target gas from a sensor resistance of the gas sensing layer. A gas detecting device includes the gas detector and a drive processing unit configured to carry out the method.

20 Claims, 9 Drawing Sheets

(56) References Cited

FOREIGN PATENT DOCUMENTS

| | | |
|---|---|---|
| JP | 2011-2358 | 1/2011 |
| JP | 2011-27752 | 2/2011 |

OTHER PUBLICATIONS

International Search Report dated Feb. 24, 2015, in corresponding International Application No. PCT/JP2014/082659.
Extended European Search Report dated Jun. 14, 2017 in corresponding European Patent Application No. 14868955.7.

* cited by examiner

1 : Si SUBSTRATE
2 : THERMAL INSULATION SUPPORTING LAYER
2a : THERMAL OXIDE SiO₂ LAYER
2b : CVD-Si₃N₄ LAYER
2c : CVD-SiO₂ LAYER
3 : HEATER LAYER
4 : ELECTRIC INSULATION LAYER
5 : GAS DETECTING UNIT
5a : BONDING LAYER
5b : SENSING LAYER ELECTRODE
5c : GAS SENSING LAYER
5d : ADSORPTION LAYER
10 GAS SENSOR

| TEMPERATURE | $T_0$ | $T_1$ | $T_2$ | $T_3$ |
|---|---|---|---|---|
| ADSORPTION LAYER | CLEANING | ADSORPTION OF TARGET GAS → CONDENSATION | THERMAL DESORPTION OF TARGET GAS → TARGET GAS MOVES TO GAS SENSING LAYER | |
| GAS SENSING LAYER (GAS DETECTING UNIT) | $O_2$ ADSORBED | $O_2$ MAINTAINED | $O_2$ DESORPTION BY REACTION WITH TARGET GAS | DETECTION OF TARGET GAS |

TEMPERATURE CHANGES IN ORDER OF $T_0$, $T_1$, $T_2$, AND $T_3$

1 : Si SUBSTRATE
2 : THERMAL INSULATION SUPPORTING LAYER
3 : HEATER LAYER
4 : ELECTRIC INSULATION LAYER
5 : GAS DETECTING UNIT
5b : SENSING LAYER ELECTRODE
5c : GAS SENSING LAYER
5d : ADSORPTION LAYER
6 : THROUGH-HOLE
7 : CAVITY

10'  GAS SENSOR

GAS DETECTING DEVICE AND METHOD THEREOF

CROSS-REFERENCE TO RELATED APPLICATIONS

This application is a continuation application, filed under 35 U.S.C. § 111(a), of International Application PCT/JP2014/082659 filed on Dec. 10, 2014, and claims benefit of foreign priority to Japanese Patent Application 2013-257735 filed Dec. 13, 2013, the disclosure of each of which is incorporated herein by reference.

BACKGROUND

1. Field

The present disclosure relates to a gas detecting device that detects gases having a concentration as low as ppb levels and a method thereof.

2. Related Art

A semiconductor gas sensor is a device that is selectively sensitive to a specific gas, such as, for example, methane gas ($CH_4$), propane gas ($C_3H_8$), butane gas ($C_4H_{10}$), or carbon monoxide (CO). The principle and structure of the semiconductor gas sensor are relatively simple, and can be mass-produced easily at low cost.

Such a semiconductor gas sensor is broadly used for detecting a gas leak and incomplete combustion. A gas leak is detected in the order of 1000 to 10000 ppm below a lower explosive limit. Incomplete combustion is detected in the order of 10 ppm to 100 ppm so that a person is not poisoned with CO.

As another use of semiconductor gas sensors, the semiconductor gas sensor is used for analyzing volatile organic compounds (hereinafter referred to simply as VOC). For example, the semiconductor gas sensor is used for analyzing VOC in an indoor environment for the purpose of preventing a sick house syndrome and analyzing VOC contained in the breath that a person exhales for the purpose of managing health conditions.

Examples of VOC include ethanol, methanol, acetone, toluene, xylene, ethyl acetate, formaldehyde, acetaldehyde, chloroform, or paradichlorobenzene contained in paint, printing ink, adhesive, detergent, gasoline, and thinner. In order to realize such analysis, it is necessary to detect VOC in the order of 0.001 to 1 ppm. However, since the conventional semiconductor gas sensor used for detecting a gas leak and incomplete combustion has insufficient sensitivity, it is difficult to detect low-concentration VOC.

Another conventional technique related to a semiconductor gas sensor that detects low-concentration gases is disclosed in patent documents Japanese Patent Application Publication No. 2011-27752 and Japanese Patent Application Publication No. 2011-2358, for example. These patent documents disclose the structure of a semiconductor gas sensor, and also disclose a technique in which a sensor is heated to high temperature and is then cooled to low temperature in order to clean interfering gases adsorbed to a gas sensing film. By doing so, the ability to sense a target gas is enhanced.

SUMMARY

However, the semiconductor gas sensors disclosed in the above patent documents are not designed to sense gases having a concentration as low as 0.001 to 1 ppm.

Thus, the present disclosure has been made in view of the above problems, and an object thereof is to provide a gas detecting device and a gas detection method capable of driving a semiconductor gas sensor so that target gases can be detected with high sensitivity and broadening a detection concentration range of target gases to a low concentration side.

In order to solve the problem, according to an aspect of the present disclosure, there is provided a gas detecting device including: a gas detecting unit having a gas sensing layer and an adsorption layer formed of a catalyst-supporting sintered material so as to cover the gas sensing layer; a heater layer that heats the gas detecting unit; and a drive processing unit that supplies current to drive the heater layer and acquires a sensor resistance from the gas sensing layer, the drive processing unit including: an oxygen adsorption unit that drives the heater layer for an oxygen adsorption period $t_0$ at an oxygen adsorption temperature $T_0$ at which oxygen is adsorbed to the gas sensing layer; a target gas adsorption unit that drives the heater layer for a target gas adsorption period $t_1$ at a target gas adsorption temperature $T_1$ at which a target gas is adsorbed to the adsorption layer after the elapse of the oxygen adsorption period $t_0$; a target gas desorption unit that drives the heater layer for a target gas desorption period $t_2$ at a target gas desorption temperature $T_2$ at which the target gas adsorbed to the adsorption layer is desorbed to move to the gas sensing layer after the elapse of the target gas adsorption period $t_1$; and a target gas concentration calculating unit that calculates a gas concentration of the target gas from the sensor resistance of the gas sensing layer after the elapse of the target gas desorption period $t_2$.

In the gas detecting device of the present disclosure, the target gas adsorption period $t_1$ is longer than the oxygen adsorption period $t_0$ and the target gas desorption period $t_2$.

In the gas detecting device of the present disclosure, the oxygen adsorption temperature $T_0$, the target gas adsorption temperature $T_1$, and the target gas desorption temperature $T_2$ are in a relation of $T_1 < T_2 \leq T_0$.

In the gas detecting device of the present disclosure, the target gas concentration calculating unit drives the heater layer for a target gas detection period $t_3$ at a target gas detection temperature $T_3$ at which the target gas is detected in the gas sensing layer after the elapse of the target gas desorption period $t_2$ and calculates the gas concentration of the target gas from the sensor resistance of the gas sensing layer in the target gas detection period $t_3$.

In the gas detecting device of the present disclosure, the target gas adsorption period $t_1$ is longer than the oxygen adsorption period $t_0$, the target gas desorption period $t_2$, and the target gas detection period $t_3$.

In the gas detecting device of the present disclosure, the oxygen adsorption temperature $T_0$, the target gas adsorption temperature $T_1$, the target gas desorption temperature $T_2$, and the target gas detection temperature $T_3$ are in a relation of $T_1 < T_3 \leq T_2 \leq T_0$ or $T_1 < T_2 \leq T_3 \leq T_0$.

According to another aspect of the present disclosure, there is provided a gas detection method including: an oxygen adsorption step of heating a gas detecting unit formed of a gas sensing layer and an adsorption layer formed of a catalyst-supporting sintered material so as to cover the gas sensing layer for an oxygen adsorption period $t_0$ at an oxygen adsorption temperature $T_0$ at which oxygen is adsorbed to the gas sensing layer; a target gas absorption step of heating the gas detecting unit for a target gas adsorption period $t_1$ at a target gas adsorption temperature $T_1$ at which a target gas is adsorbed to the adsorption layer after the end of the oxygen adsorption step; a target gas desorption step of heating the gas detecting unit for a target gas desorption period $t_2$ at a target gas desorption temperature $T_2$ at which the target gas adsorbed to the adsorption layer is desorbed to move to the gas sensing layer after the end of the target gas absorption step; and a target gas concentration calculating step of calculating a gas concentration of the target gas from a sensor resistance of the gas sensing layer after the end of the target gas desorption step.

In the gas detection method of the present disclosure, the target gas adsorption period $t_1$ is longer than the oxygen adsorption period $t_0$ and the target gas desorption period $t_2$.

In the gas detection method of the present disclosure, the oxygen adsorption temperature $T_0$, the target gas adsorption temperature $T_1$, and the target gas desorption temperature $T_2$ are in a relation of $T_1 < T_2 \leq T_0$.

In the gas detection method of the present disclosure, the target gas concentration calculating step involves heating the gas detecting unit for a target gas detection period $t_3$ at a target gas detection temperature $T_3$ at which the target gas is detected in the gas sensing layer after the elapse of the target gas desorption period $t_2$, and calculating the gas concentration of the target gas from the sensor resistance of the gas sensing layer in the target gas detection period $t_3$.

In the gas detection method of the present disclosure, the target gas adsorption period $t_1$ is longer than the oxygen adsorption period $t_0$, the target gas desorption period $t_2$, and the target gas detection period $t_3$.

In the gas detection method of the present disclosure, the oxygen adsorption temperature $T_0$, the target gas adsorption temperature $T_1$, the target gas desorption temperature $T_2$, and the target gas detection temperature $T_3$ are in a relation of $T_1 < T_3 \leq T_2 \leq T_0$ or $T_1 < T_2 \leq T_3 \leq T_0$.

According to the present disclosure, it is possible to provide a gas detecting device capable of driving a semiconductor gas sensor so that target gases can be detected with high sensitivity and broadening a detection concentration range of target gases to a low concentration side and to provide a method thereof.

BRIEF DESCRIPTION OF THE DRAWINGS

These and/or other aspects and advantages will become apparent and more readily appreciated from the following description of the embodiments, taken in conjunction with the accompanying drawings of which:

FIGS. 7A though 7C are explanatory diagrams for describing a gas sensor of a gas detecting device according to another embodiment of the present disclosure, in which FIG. 7A is a plan view of a gas sensor.

DESCRIPTION OF EMBODIMENTS

Figure 1:
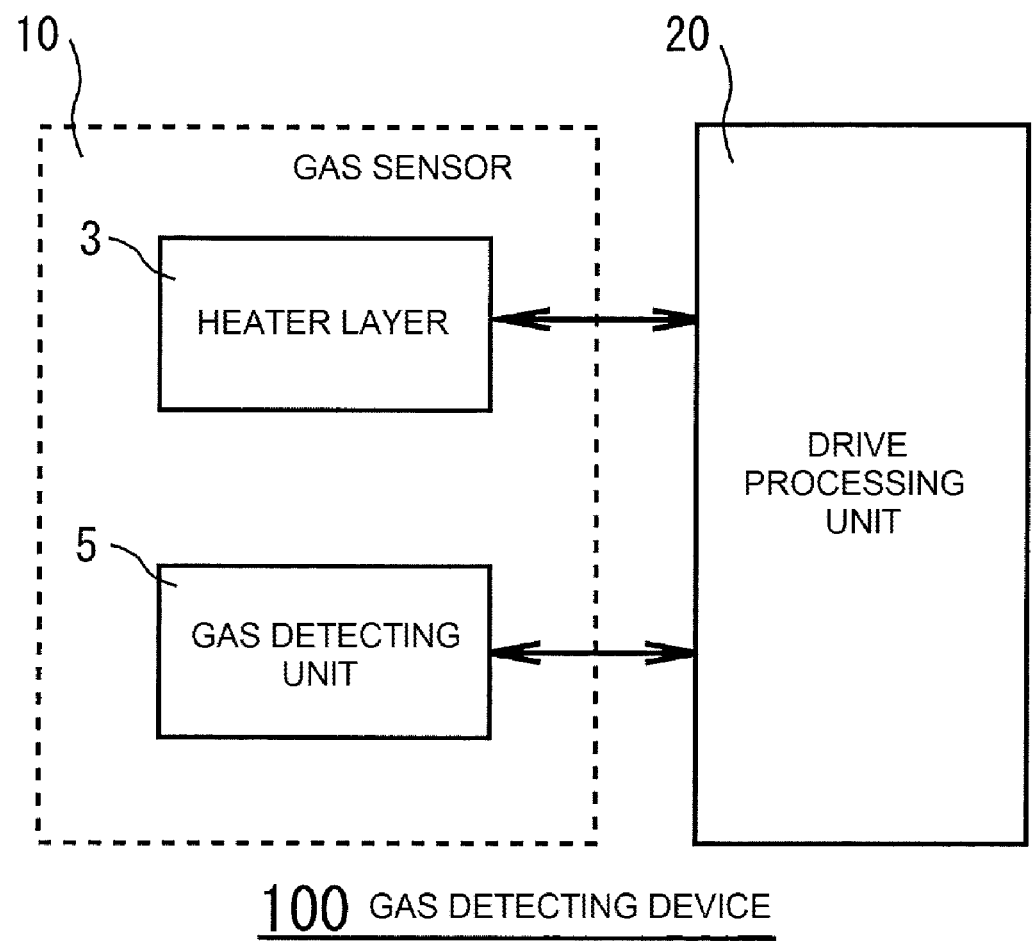
FIG. 1 is a circuit block diagram of main parts of a gas detecting device according to an embodiment of the present disclosure.

Next, a gas detecting device and a gas detection method according to an embodiment of the present disclosure will be described with reference to the drawings. As illustrated in FIG. 1, a gas detecting device 100 includes at least a gas sensor 10 and a drive processing unit (or drive device, or drive processor) 20. The drive processing unit 20 may include an operation input unit, a display unit that displays a gas concentration of a target gas, and the like.

Figure 2:
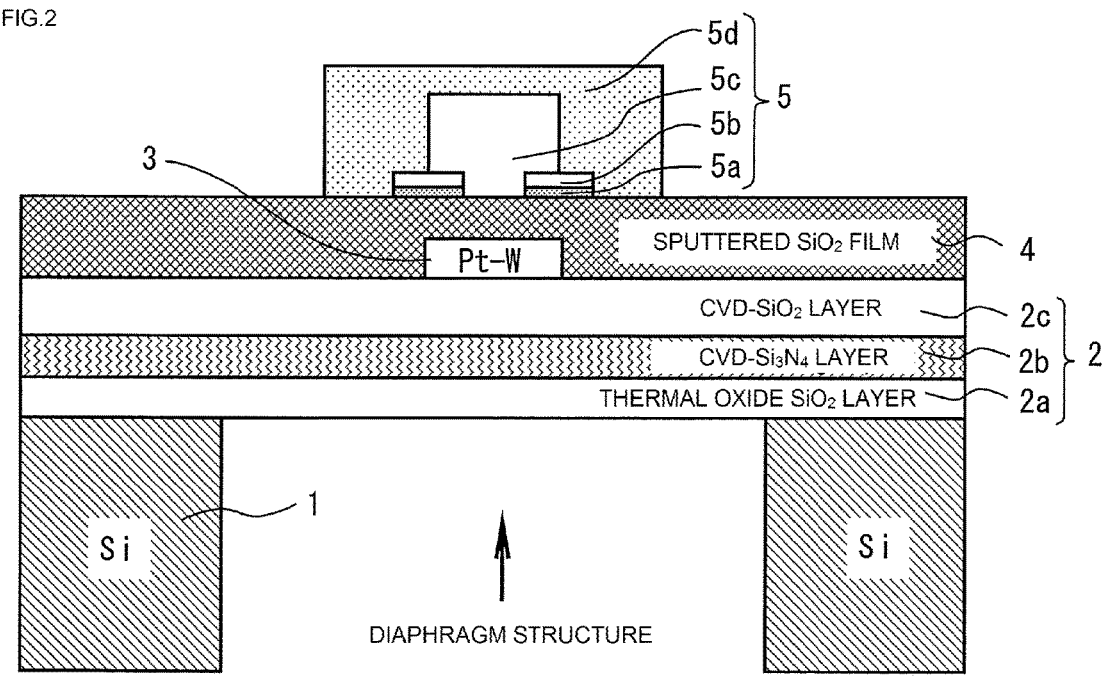
FIG. 2 is a longitudinal sectional view schematically illustrating a gas sensor.

The gas sensor 10 is a semiconductor sensor, and as illustrated in FIG. 2, further includes a silicon substrate (hereinafter referred to as a Si substrate) 1, a thermal insulation supporting layer 2, a heater layer 3, an electric insulation layer 4, and a gas detecting unit 5. While FIG. 2 illustrates the configuration of a thin-film semiconductor gas sensor schematically for simplicity and clarity of illustration, the size, thickness, and the like of the respective units are not drawn to scale.

Specifically, the gas detecting unit 5 includes a bonding layer 5a, a sensing layer electrode 5b, a gas sensing layer 5c, and an adsorption layer 5d. In the present embodiment, the gas sensing layer 5c is a stannic oxide layer (hereinafter referred to as a $SnO_2$ layer), for example. Moreover, in the present embodiment, the adsorption layer 5d is an alumina sintered material (hereinafter referred to as a catalyst supporting $Al_2O_3$ sintered material) that supports a palladium oxide (PdO) as a catalyst.

The surfaces of the electric insulation layer 4, the bonding layer 5a, a pair of sensing layer electrodes 5b, and the gas sensing layer 5c are covered by the adsorption layer 5d. As illustrated in FIG. 1, the heater layer 3 is electrically connected to the drive processing unit 20, and the drive processing unit 20 drives the heater layer 3. Moreover, the gas detecting unit 5 (specifically, the gas sensing layer 5c with the sensing layer electrode 5b interposed) is electrically connected to the drive processing unit 20, and the drive processing unit 20 reads a sensor resistance of the gas sensing layer 5c.

Next, the configuration of respective units will be described. The Si substrate 1 is formed of silicon (Si) and a through-hole is formed in a portion immediately below the gas detecting unit 5. The thermal insulation supporting layer 2 is formed as a diaphragm which is attached to an opening of the through-hole and is provided on the Si substrate 1.

Specifically, the thermal insulation supporting layer 2 has a three-layer structure including a thermal oxide $SiO_2$ layer 2a, a CVD-$Si_3N_4$ layer 2b, and a CVD-$SiO_2$ layer 2c.

The thermal oxide $SiO_2$ layer 2a is formed as a thermal insulation layer and has a function of decreasing thermal capacity so that heat generated by the heater layer 3 is not transmitted to the Si substrate 1. Moreover, the thermal oxide $SiO_2$ layer 2a has high resistance against plasma etching and facilitate formation of a through-hole in the Si substrate 1 by plasma etching, which will be described later.

The CVD-$Si_3N_4$ layer 2b is formed above the thermal oxide $SiO_2$ layer 2a.

The CVD-$SiO_2$ layer 2c improves adhesion to the heater layer 3 and secures electrically insulation. The $SiO_2$ layer formed by CVD (chemical vapor deposition) has small internal stress.

The heater layer 3 is a thin Pt—W film and is provided on an upper surface approximately at the center of the thermal insulation supporting layer 2. Moreover, a power supply line is also formed. This power supply line is connected to the drive processing unit 20 as illustrated in FIG. 1.

The electric insulation layer 4 is a sputtered $SiO_2$ layer that secures electrical insulation and is provided so as to cover the thermal insulation supporting layer 2 and the heater layer 3. The electric insulation layer 4 secures electrical insulation between the heater layer 3 and the sensing layer electrode 5b. Moreover, the electric insulation layer 4 improves adhesion to the gas sensing layer 5c.

The bonding layer 5a is a Ta (tantalum) film or a Ti (titanium) film, for example, and a pair of left and right bonding layers 5a is provided on the electric insulation layer 4. The bonding layer 5a is interposed between the sensing layer electrode 5b and the electric insulation layer 4 so as to enhance bonding strength. The sensing layer electrode 5b is a Pt (platinum) film or an Au (gold) film, for example, and a pair of left and right sensing layer electrodes 5b is provided as a sensing electrode of the gas sensing layer 5c. The gas sensing layer 5c is a $SnO_2$ layer and is formed on the electric insulation layer 4 so as to bridge the pair of sensing layer electrodes 5b. In the present embodiment, although the gas sensing layer 5c is an $SnO_2$ layer, the gas sensing layer 5c may be a thin layer that contains, as its main components, a metal oxide such as $In_2O_3$, $WO_3$, ZnO, or $TiO_2$ in addition to $SnO_2$.

The adsorption layer 5d is a sintered material that supports a palladium oxide (PdO) and is a catalyst supporting $Al_2O_3$ sintered material as described above. Since $Al_2O_3$ is a porous material, the chance of gases passing through holes to contact PdO increases. Moreover, $Al_2O_3$ accelerates combustion reaction of reducing gases (interfering gases) that have stronger oxidization activity than a target gas to be sensed, and the selectivity of target gas (VOC contained in exhaled breath and indoor environment, for example, ethanol and acetone) increases. That is, it is possible to oxidize and remove interfering gases from a target gas (VOC).

The adsorption layer 5d may contain, as its main components, a metal oxide such as $Cr_2O_3$, $Fe_2O_3$, $Ni_2O_3$, $ZrO_2$, $SiO_2$, or zeolite in addition to $Al_2O_3$. The adsorption layer 5d is provided so as to cover the surfaces of the electric insulation layer 4, the bonding layer 5a, the pair of sensing layer electrodes 5b, and the gas sensing layer 5c.

The gas sensor 10 has a diaphragm structure so as to have high thermal insulating properties and low thermal capacity. Moreover, the gas sensor 10 has the sensing layer electrode 5b, the gas sensing layer 5c, the adsorption layer 5d, and the heater layer 3 which are formed using technique such as MEMS (microelectromechanical system) as to decrease thermal capacity. Due to this, a change with time in temperature from $T_1$ to $T_2$ is accelerated and thermal desorption occurs in a very short time, which will be described later. Thus, the gas concentration of a target gas reaching the gas sensing layer 5c increases, and the gas sensor 10 having higher sensitivity is obtained.

Next, an outline of a method for manufacturing the gas sensor 10 and the gas detecting device 100 according to the present embodiment will be described.

First, one surface (or both front and rear surfaces) of a planar silicon wafer (not illustrated) is thermally oxidized according to a thermal oxidization method to form the thermal oxide $SiO_2$ layer 2a which is a thermal oxide $SiO_2$ film. A CVD-$Si_3N_4$ film serving as a supporting film is deposited on an upper surface on which the thermal oxide $SiO_2$ layer 2a is formed according to a plasma CVD method to form the CVD-$Si_3N_4$ layer 2b. Moreover, a CVD-$SiO_2$ film serving as a thermal insulation film is deposited on an upper surface of the CVD-$Si_3N_4$ layer 2b according to a plasma CVD method to form the CVD-$SiO_2$ layer 2c.

Further, a Pt—W film is deposited on an upper surface of the CVD-$SiO_2$ layer 2c according to a sputtering method to form the heater layer 3. Moreover, a sputtered $SiO_2$ film is deposited on the upper surfaces of the CVD-$SiO_2$ layer 2c and the heater layer 3 according to a sputtering method to form the electric insulation layer 4 which is a sputtered $SiO_2$ layer.

The bonding layer 5a and the sensing layer electrode 5b are formed on the electric insulation layer 4. Deposition is performed according to a general sputtering method using an RF magnetron sputtering apparatus. The same deposition conditions are used for the bonding layer (Ta or Ti) 5a and the sensing layer electrode (Pt or Au) 5b such that an Ar (argon) gas pressure is 1 Pa, a substrate temperature is 300° C., RF power is 2 W/cm$^2$, and a film thickness is 500 Å and 2000 Å for the bonding layer 5a and the sensing layer electrode 5b, respectively.

A $SnO_2$ film is deposited on the electric insulation layer 4 so as to be bridged across the pair of sensing layer electrodes 5b according to a sputtering method to form the gas sensing layer 5c. In this case, deposition is performed according to a reactive sputtering method using an RF magnetron sputtering apparatus. As a target, $SnO_2$ that contains 0.1 wt % of Sb is used. Deposition is performed under such conditions that an $Ar+O_2$ gas pressure is 2 Pa, a substrate temperature is 150° C. to 300° C., RF power is 2 W/cm$^2$, and a film thickness is 400 nm. The gas sensing layer 5c is formed in a square form of which one side is approximately 50 μm in a plan view.

Subsequently, the adsorption layer 5d is formed. In forming of the adsorption layer 5d, first, 7.0 wt % of diethylene glycol monoethyl ether and 5 to 20 wt % of silica sol binder are added to γ-alumina (average grain size of 2 to 3 μm) in which 7.0 wt % of PdO is added to form a paste. Moreover, an adsorption film is formed to a thickness of approximately 30 μm according to screen printing. After that, this film is baked at high temperature of 500° C. for 12 hours. In this case, the diameter of the adsorption layer 5d is larger than the outer circumference of the gas sensing layer 5c so as to sufficiently cover the gas sensing layer 5c. The adsorption layer 5d is formed in a circular form having a diameter of approximately 200 μm in a plan view.

Finally, a micro-fabrication process of removing silicon from the rear surface of the silicon wafer (not illustrated) by etching is performed to form the Si substrate 1 having through-holes. In this way, the gas sensor 10 having a diaphragm structure is obtained. Further, the heater layer 3 and the sensing layer electrode 5b are electrically connected to the drive processing unit 20. In this way, the gas sensor 10 and the gas detecting device 100 are manufactured.

Figure 3:
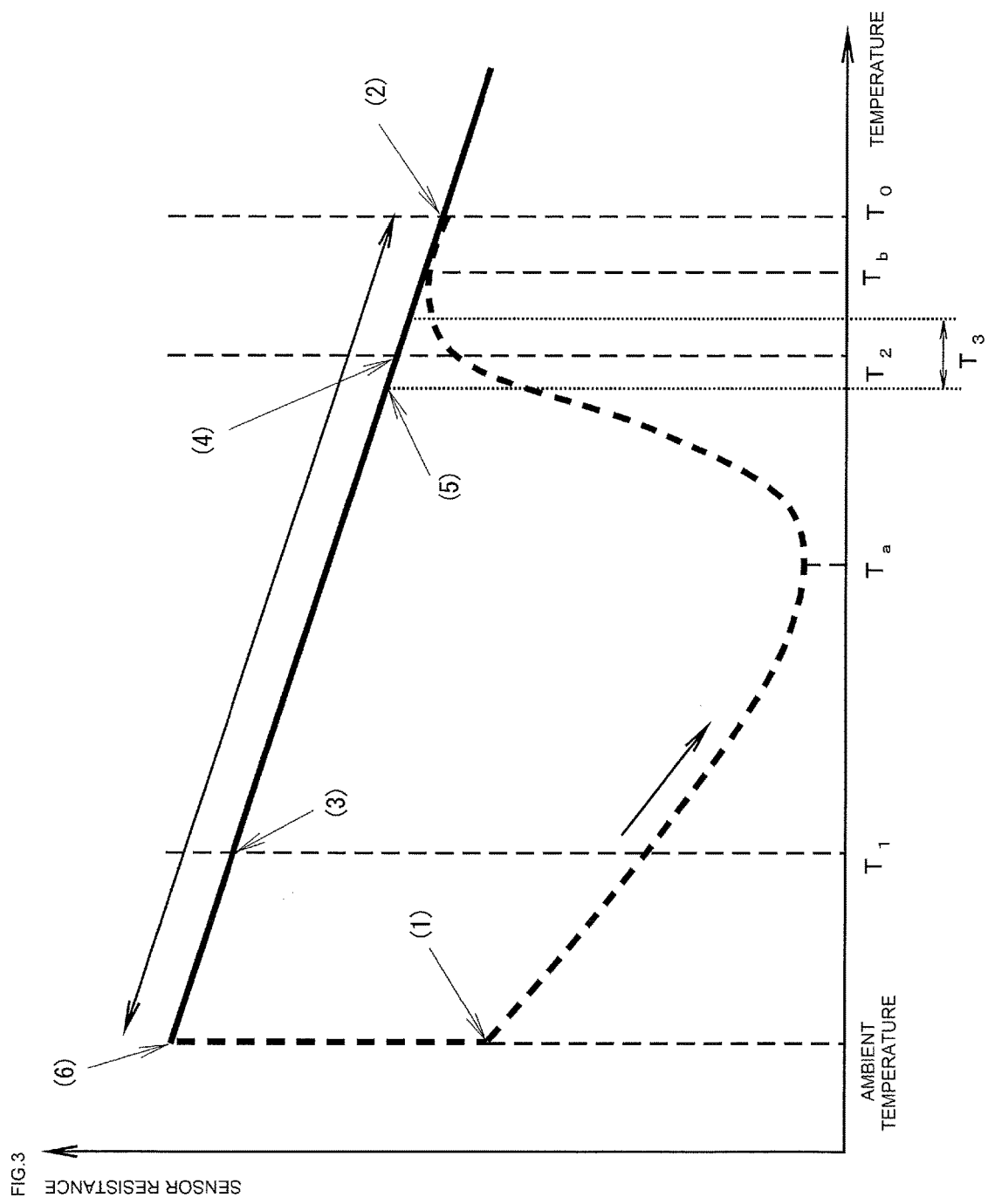
FIG. 3 is a temperature-sensor resistance characteristic diagram of a gas sensing layer.

Next, the principle of detecting low-concentration gases using the gas detecting device 100 according to the present disclosure and the gas detecting method thereof will be described. First, the present inventor has found based on experimental results that the sensor resistance (voltage V1)

of the gas sensing layer 5c and the temperature of the heater layer 3 have such a correlation as illustrated in FIG. 3.

The graph in FIG. 3 is a temperature profile which shows the relation between the resistance (sensor resistance: vertical axis) of the gas sensing layer 5c and the temperature (horizontal axis) of the heater layer 3 in the normal air (that is, in an environment where no target gas is present therearound). Further, in FIG. 3, a broken line illustrates the temperature profile in a normal state before oxygen saturates and a solid line illustrates the temperature profile immediately after oxygen saturates.

When the temperature of the heater layer 3 increases from an ambient temperature to temperature $T_a$, as indicated by the broken line in FIG. 3, the sensor resistance of the gas sensing layer 5c which is a thin $SnO_2$ film decreases with an increase in temperature. The reason why the sensor resistance of the gas sensing layer 5c decreases in a temperature region where the temperature increases up to $T_a$ is because "oxygen desorption" occurs with an increase in temperature. In "oxygen desorption," ions ($O^{2-}$) adhering the thin $SnO_2$ film give electrons to the thin $SnO_2$ film when the ions desorbed from the thin $SnO_2$ film. That is, the sensor resistance decreases due to an increase in the number of electrons.

When the temperature of the heater layer 3 increases further to exceed the temperature $T_a$, the sensor resistance of the gas sensing layer 5c increases in an increase in temperature. The reason why the sensor resistance increases in a temperature region where the temperature increases from $T_a$ to $T_b$ is because "oxygen adsorption" (negative charge adsorption) occurs in the thin $SnO_2$ film, which is a reverse phenomenon of the "oxygen desorption". In the negative charge adsorption, when $O_2$ is adsorbed to the thin $SnO_2$ film, $O_2$ deprives electrons from the thin $SnO_2$ film and the electrons adhere the thin $SnO_2$ film in the form of ions ($O^{2-}$). As a result, the resistance of the thin $SnO_2$ film increases. That is, the sensor resistance increases due to a decrease in the number of electrons.

The "oxygen adsorption" ends at temperature $T_b$, and when the temperature of the heater layer 3 increases further to exceed $T_b$, as indicated by an overlapping portion of the broken line and solid line in FIG. 3, the sensor resistance of the gas sensing layer 5c decreases with an increase in temperature. It is considered that the reason why the sensor resistance decreases in a temperature region where temperature is higher than $T_b$ is because, although oxygen saturates due to adsorption in the temperature region higher than $T_b$, the sensor resistance decreases with an increase in temperature due to characteristics of semiconductor ($SnO_2$). The behavior of the temperature profile indicated by the broken line has been described. Since VOC which is a target gas is not present, oxygen is not consumed in the gas sensing layer 5c, and the sensor resistance changes along the temperature profile indicated by the solid line in FIG. 3 in a further change in temperature. The temperature profile in an environment where no target gas is present is as illustrated in FIG. 3.

When VOC which is a target gas is present, oxygen is consumed from the gas sensing layer 5c which is a thin $SnO_2$ film by the VOC, and "oxygen desorption" occurs and the number of free electrons in the gas sensing layer 5c increases. Moreover, the sensor resistance decreases with the gas concentration of the VOC which is a target gas.

Figure 4:
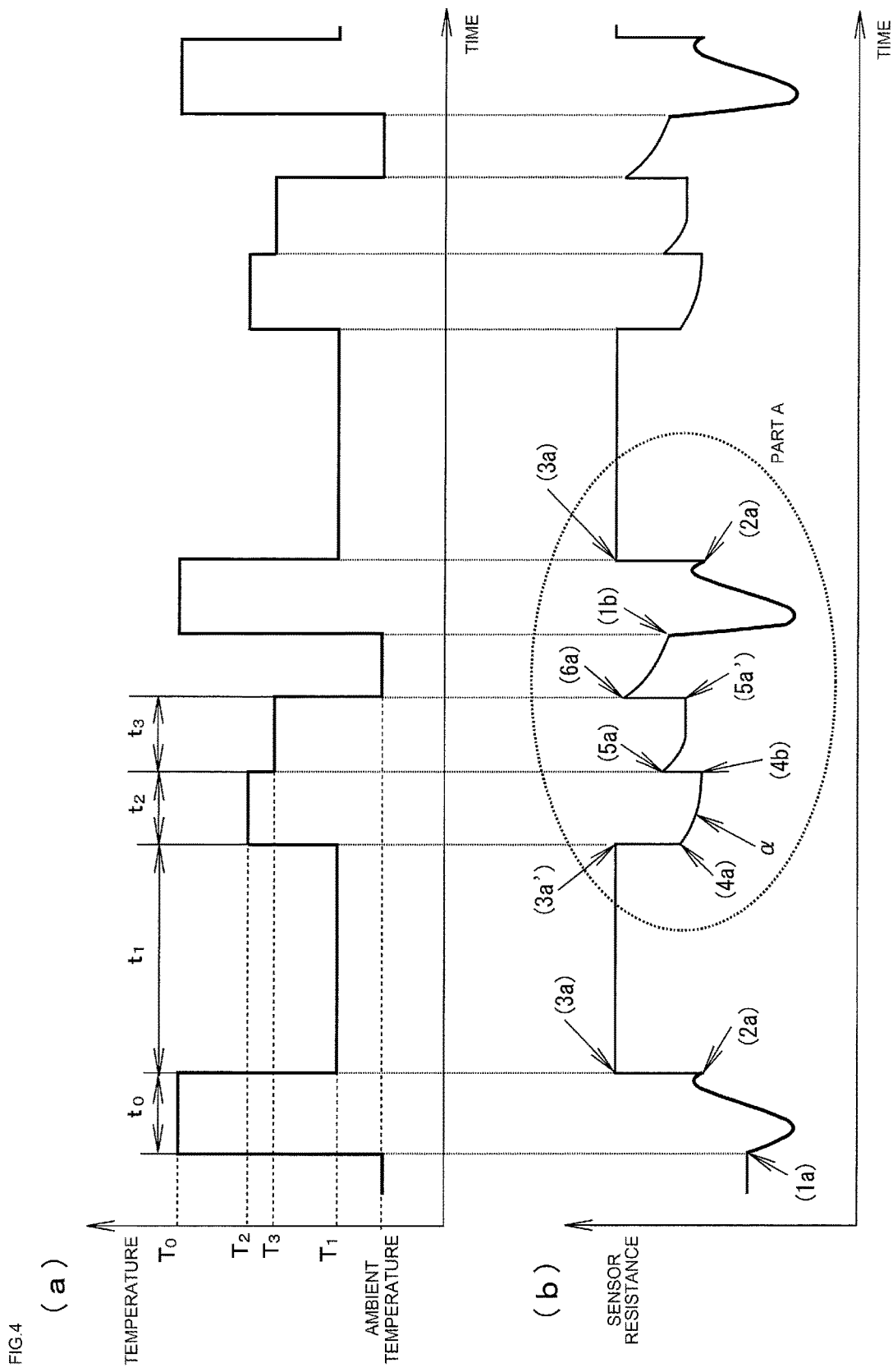
FIG. 4, part (a) and part (b), are explanatory diagrams for describing a relation between a heater layer temperature and a sensor resistance, in which part (a) is a driving pattern diagram for describing a heater layer driving scheme and part (b) is a sensor resistance characteristic diagram for describing a sensor resistance corresponding to driving of a heater layer.

In the present disclosure, low-concentration gases are detected according to the following principle. FIG. 4, part (a) and part (b), are explanatory diagrams for describing the relation between a heater layer temperature and a sensor resistance, in which FIG. 4, part (a), is a driving pattern diagram for describing a heater layer driving scheme and FIG. 4, part (b), is a sensor resistance characteristic diagram for describing a sensor resistance corresponding to driving of a heater layer. It is assumed that the gas sensor 10 is in an atmosphere that includes VOC which is a target gas. The part A in FIG. 4, part (b), is illustrated in an enlarged view in FIG. 5. The points (1), (2), (3), (4), (5), and (6) in the temperature profile of FIG. 3 described above correspond to the points (1a), (2a), (3a), (4a), (5a), and (6a) in FIG. 4, part (b). FIG. 3 illustrates the behavior when VOC which is a target gas is not present whereas FIG. 4, part (b), illustrates the behavior when VOC which is a target gas is present by a solid line unlike FIG. 3.

Figures 5, 6:
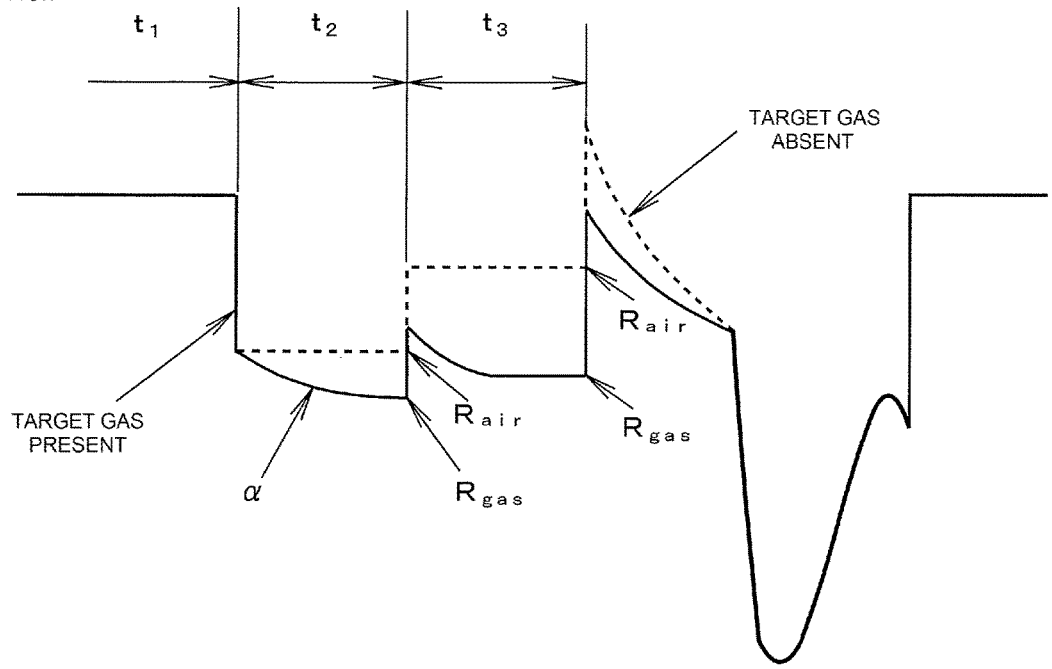
FIG. 5 is an enlarged view of part A in the sensor resistance characteristic diagram.
FIG. 6 is an explanatory diagram for describing the state of an adsorption layer and a gas sensing layer depending on temperature.

As illustrated in FIG. 4, part (a), when the heater layer 3 is driven so that the temperature thereof sequentially reaches an oxygen adsorption temperature $T_0$, a target gas adsorption temperature $T_1$, a target gas desorption temperature $T_2$, and a target gas detection temperature $T_3$, a phenomenon as illustrated in FIG. 6 occurs in the gas sensing layer 5c and the adsorption layer 5d. The phenomenon will be described for respective temperatures.

First, as illustrated in FIG. 4, part (a), the heater is driven so that the temperature is increased from ambient temperature to the oxygen adsorption temperature $T_0$ and the oxygen adsorption temperature $T_0$ is maintained for an oxygen adsorption period $t_0$. As illustrated in FIG. 4, part (b), when the temperature is increased from ambient temperature to the oxygen adsorption temperature $T_0$, the sensor resistance of the gas sensing layer 5c changes from point (1a) in FIG. 4, part (b), to point (2a) according to such a behavior as a curved line. The oxygen adsorption temperature $T_0$ is a temperature at which sufficient "oxygen adsorption" (negative charge adsorption) occurs in the thin $SnO_2$ film, and is near the temperature $T_b$ of 320° C., for example.

In this case, as illustrated in FIG. 6, an oxygen adsorption reaction occurs in the gas sensing layer 5c, oxygen is adsorbed to the gas sensing layer 5c, and the sensor resistance increases. Further, an oxidizing action of catalyst occurs in the adsorption layer 5d, and the gases adhering the surface of the adsorption layer 5d are combusted temporarily and cleaned. After the elapse of the oxygen adsorption period $t_0$, gases are not adsorbed to the adsorption layer 5d, and a sufficient amount of oxygen is adsorbed to the gas sensing layer 5c.

Subsequently, as illustrated in FIG. 4, part (a), the heater is driven so that the temperature is decreased to the target gas adsorption temperature $T_1$ sufficiently lower than the oxygen adsorption temperature $T_0$, and the target gas adsorption temperature $T_1$ is maintained for a target gas adsorption period $t_1$. As illustrated in FIG. 4, part (a), when the temperature is decreased instantly from the oxygen adsorption temperature $T_0$ to the target gas adsorption temperature $T_1$, the sensor resistance changes from the point (2a) in FIG. 4, part (b), to the point (3a) according to such a behavior as a straight line. During the target gas adsorption period $t_1$, the sensor resistance moves to the point (3a') while maintaining the same value. The target gas adsorption temperature $T_1$ is a temperature at which a target gas is adsorbed to the adsorption layer 5d without being combusted in particular, and is near an ambient temperature of 20° C., for example. In this case, condensation of a target gas component occurs in the adsorption layer 5d due to, for example, capillary condensation.

When the target gas adsorption period $t_1$ is increased, although a larger amount of target gas is adsorbed to the adsorption layer 5d, since oxygen starts being desorbed from the gas sensing layer $5c$ at the target gas adsorption temperature $T_1$, it is not possible to increase the target gas adsorption period $t_1$ without restriction. Thus, the target gas adsorption period $t_1$ is selected such that the amount of target gas adsorbed to the adsorption layer $5d$ reaches an equilibrium condition and a large amount of oxygen is not desorbed from the gas sensing layer $5c$.

When the temperature of the heater layer 3 is decreased to the target gas adsorption temperature $T_1$ and the target gas adsorption temperature $T_1$ is maintained for the target gas adsorption period $t_1$ in which the target gas is adsorbed to the adsorption layer $5d$, as illustrated in FIG. 6, a high-concentration target gas is adsorbed to the adsorption layer $5d$ while maintaining a high sensor resistance state in the gas sensing layer $5c$ (that is, a state in which a sufficient amount of oxygen is adsorbed to the gas sensing layer $5c$).

Subsequently, as illustrated in FIG. 4, part (a), the heater is driven so that the temperature is increased to the target gas desorption temperature $T_2$ sufficiently higher than the target gas adsorption temperature $T_1$ and the target gas desorption temperature $T_2$ is maintained for a target gas desorption period $t_2$. The target gas desorption temperature $T_2$ is a temperature of approximately 320° C. similarly to $T_0$, for example. As illustrated in FIG. 4, part (b), when the temperature is increased instantly from the target gas adsorption temperature $T_1$ to the target gas desorption temperature $T_2$, the sensor resistance changes from the point (3a') in FIG. 4, part (b), to the point (4a) according to such a behavior as a straight line. By doing so, as illustrated in FIG. 6, at the target gas desorption temperature $T_2$, thermal desorption of a target gas component condensed to the adsorption layer $5d$ occurs, and the target gas reaches the gas sensing layer $5c$ in a higher concentration than the original gas concentration in the air. The target gas reacts with oxygen in the gas sensing layer $5c$, and oxygen is desorbed so that the sensor resistance starts decreasing. As a result, the sensor resistance changes from the point (4a) in FIG. 4, part (b), to the point (4b) according to such a behavior as a curve a.

After that, as illustrated in FIG. 4, part (a), the heater is driven so that the gas sensing layer $5c$ is maintained at the target gas detection temperature $T_3$ for a target gas detection period $t_3$. As illustrated in FIG. 4, part (b), when the temperature is decreased instantly from the target gas desorption temperature $T_2$ to the target gas detection temperature $T_3$, the sensor resistance changes from the point (4b) in FIG. 4, part (b), to the point (5a) according to such a behavior as a straight line. During the target gas detection period $t_3$, the sensor resistance moves to the point (5a') while converging to a constant value along a curve. This curve illustrates a state in which the target gas reacts with oxygen at first so that the oxygen is desorbed and the sensor resistance decreases, and after the elapse of a short period, the target gas is not present, desorption of oxygen stops, and the sensor resistance reaches a constant value. As illustrated in FIG. 6, gas detection starts after the elapse of the target gas detection period $t_3$. In this manner, gas detection is enabled even in a case where low-concentration VOC is detected.

After that, as illustrated in FIG. 4, part (a), after gases are detected, the heater is driven so that the temperature decreases down to the ambient temperature. As illustrated in FIG. 4, part (b), when the temperature is decreased instantly from the target gas detection temperature $T_3$ to the ambient temperature, the sensor resistance changes from the point (5a') in FIG. 4, part (b), to the point (6a) according to such a behavior as a straight line. The sensor resistance decreases further to move up to the point (1b).

Subsequently, when the temperature is increased from the ambient temperature to the oxygen adsorption temperature $T_0$, the sensor resistance changes from the point (1b) in FIG. 4, part (b), to the point (2a) according to such a behavior as a curve. When the driving pattern of FIG. 4, part (a), is performed repeatedly, the sensor resistance changes along the solid line in FIG. 4, part (b). After that, the same behavior appears repeatedly. When a target gas is present, the target gas is detected using the fact that the sensor resistance decreases according to the behavior from the point (4a) to the point (4b) indicated by arrow α. When a sufficient period elapses without driving the heater after the sensor resistance reaches the point (6a) (that is, after the driving is stopped), the sensor resistance returns to the point (1a) rather than the point (1b).

Here, since the amount of target gas adsorbed to the adsorption layer $5d$ is determined by the adsorption equilibrium of the target gas in the air, the amount of adsorbed target gas has a certain relation with the gas concentration in the air. Thus, even when the sensitivity is increased with the above-described mechanism, a certain relation is obtained between the gas concentration in the air and the output of the gas sensor. The VOC gas is detected using such a behavior.

Subsequently, a gas detection method and the details of the special driving scheme of the heater layer 3 will be described with reference to FIG. 4 to FIG. 6. The gas detecting device 100 of the present disclosure drives VOC according to a special driving scheme for VOC detection to improve VOC concentration detection sensitivity.

The drive processing unit 20 functions as an oxygen adsorption step of driving the heater layer 3 for the oxygen adsorption period $t_0$ at the oxygen adsorption temperature $T_0$ at which oxygen is adsorbed to the gas sensing layer $5c$. When the drive processing unit 20 does not supply a driving current signal to maintain the heater temperature of the heater layer 3 to a high-temperature state (for example, 320° C.) for a predetermined period (for example, 0.6 s), oxygen is adsorbed to the gas sensing layer $5c$ as illustrated in FIG. 6. Further, an oxidizing action of catalyst occurs in the adsorption layer $5d$, and the gases adhering the surface of the adsorption layer $5d$ are combusted temporarily and cleaned.

Subsequently, the drive processing unit 20 functions as a target gas adsorption step of driving the heater layer 3 for the target gas adsorption period $t_1$ at the target gas adsorption temperature $T_1$ at which the target gas is adsorbed to the adsorption layer $5d$. The target gas adsorption temperature $T_1$ is an outside ambient temperature during measurement, and is an ambient temperature of 20° C., for example. The drive processing unit 20 supplies a driving signal to the heater layer 3 for a predetermined period (for example, 20 s) or a very short period. By doing so, VOC adheres the adsorption layer $5d$ for a period in which the sensor temperature is substantially at the room temperature as illustrated in FIG. 6. Although the target gas adsorption period $t_1$ is long, since substantially no or small current flows, the power consumption rarely increases.

Subsequently, the drive processing unit 20 functions as a target gas desorption step of driving the heater layer 3 for the target gas desorption period $t_2$ at the target gas desorption temperature $T_2$ at which the target gas is desorbed from the adsorption layer $5d$ and moves to the gas sensing layer $5c$. When the drive processing unit 20 supplies a driving current signal to maintain the heater temperature of the heater layer 3 to a high-temperature state (for example, 320° C. or 300° C.) for a predetermined period (for example, 0.6 s). By doing so, as illustrated in FIG. 6, the VOC from the adsorption layer $5d$ reacts with the oxygen adsorbed to the gas sensing layer 5c, whereby the oxygen is desorbed from the gas sensing layer 5c. As a result, the sensor resistance of the gas sensing layer 5c changes.

Subsequently, the drive processing unit 20 functions as a target gas detection step of detecting the sensor resistance of the gas sensing layer 5c at the target gas detection temperature $T_3$ after the elapse of the predetermined period $t_3$ and calculating the gas concentration from the sensor resistance. In this way, as illustrated in FIG. 6, the gas concentration of low-concentration VOC is detected. The oxygen adsorption step, the target gas adsorption step, the target gas desorption step, and the target gas detection step may be performed repeatedly to obtain a stable sensor resistance with a small variation, and thereafter, the VOC concentration may be detected. The gas detecting device 100 detects gases in this manner.

Here, the oxygen adsorption temperature $T_0$, the target gas adsorption temperature $T_1$, the target gas desorption temperature $T_2$, and the target gas detection temperature $T_3$ are in the relation of $T_1 < T_3 \leq T_2 \leq T_0$. However, a relation of $T_1 < T_2 < T_3 \leq T_0$ may be used. A temperature relation determining method will be described. In FIG. 5 which is an enlarged view of part A in FIG. 4, part (b), the behavior of a sensor resistance when a target gas is present is depicted by a solid line, and the behavior of a sensor resistance when a target gas is not present is depicted by a broken line. In particular, between the target gas desorption period $t_2$ and the target gas detection period $t_3$, the resistance is different depending on the presence of a target gas.

As illustrated in FIG. 5, a resistance change rate $R_3$ ($R_3 = R_{air}/R_{gas}$) when a target gas is present (solid line) and is not (broken line) in the target gas detection period $t_3$ is calculated (the resistance change rate $R_2$ in the target gas desorption period $t_2$ is not taken into consideration). A large resistance change rate $R_3$ means a high gas sensitivity, and a low-concentration gas is detected reliably by measuring gases with as high a gas sensitivity as possible. The $R_3$ for $T_1 < T_3 \leq T_2 \leq T_0$ is compared with the $R_3$ for $T_1 < T_2 \leq T_3 \leq T_0$, and a temperature relation is selected so that the resistance change rate $R_3$ has a large value. Gases can be detected with high sensitivity by employing a temperature relation in which a large resistance change rate $R_3$ is obtained. In the present embodiment, the relation of $T_1 < T_3 \leq T_2 \leq T_0$ is employed. This temperature relation changes depending on the type of the gas sensing layer.

Moreover, a resistance change rate $R_2$ ($R_2 = R_{air}/R_{gas}$) when a target gas is present (solid line) and is not (broken line) in the target gas desorption period $t_2$ is also calculated. If $R_3 \leq R_2$ is satisfied always regardless of the target gas detection temperature $T_3$, it is meaningless to employ the target gas detection temperature $T_3$ and it is reasonable to include the target gas detection period $t_3$ in the target gas desorption period $t_2$ (see Example 1 described later). In this case, gases can be detected with high sensitivity using the largest resistance change rate $R_2$. In this case, the relation of $T_1 < T_2 \leq T_0$ is employed. This temperature relation also changes depending on the type of the gas sensing layer. The gas detecting device 100 can be configured in this manner.

In the gas detecting device 100 described above, the oxygen adsorption temperature $T_0$ is set to be high in particular so as to maximize the oxygen adsorption amount. Moreover, the target gas adsorption temperature $T_1$ is set to be sufficiently low and the target gas adsorption period $t_1$ is set to be longer than the oxygen adsorption period $t_0$, the target gas desorption period $t_2$, and the target gas detection period $t_3$ so that a large amount of target gas is adsorbed to the adsorption layer 5d. By doing so, the amount of oxygen consumed by the target gas increases, the change in the sensor resistance increases, and the detection sensitivity can be increased.

Figure 7A:
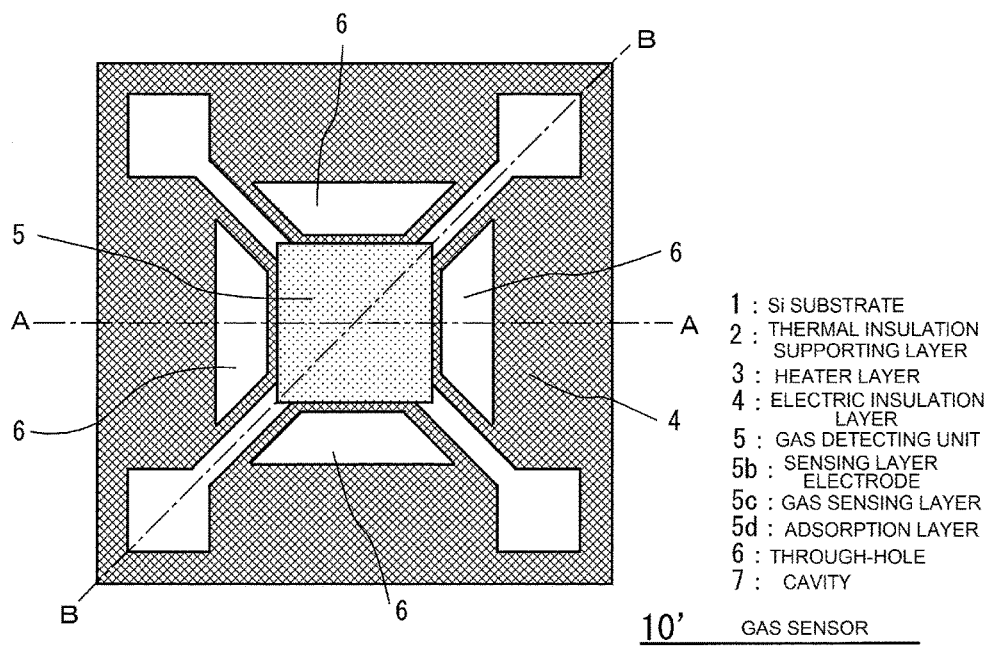
Figure 7B:
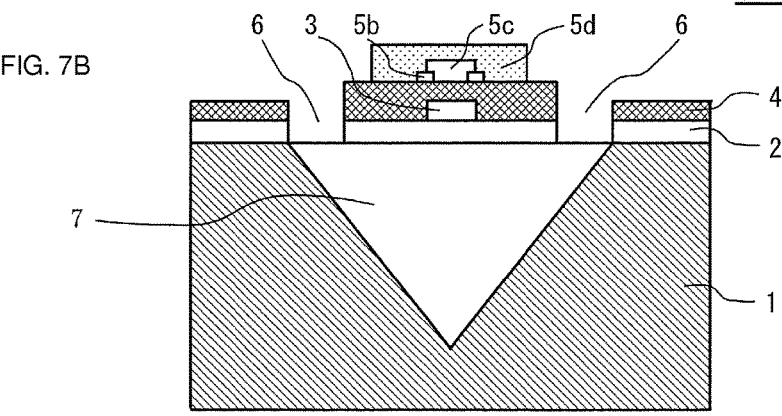
FIG. 7B is a sectional view along line A-A of the gas sensor.
Figure 7C:
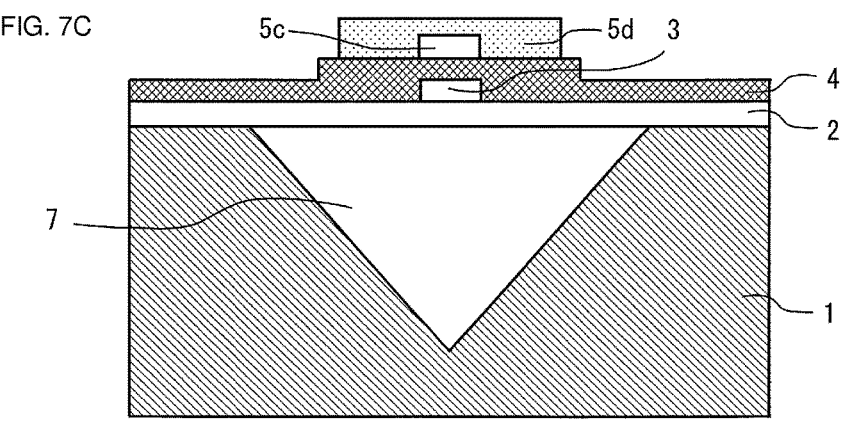
FIG. 7C is a sectional view along line B-B of the gas sensor.

Next, another embodiment of the present disclosure will be described with reference to the drawings. As compared to the above-described embodiment, this embodiment employs a gas sensor 10' having such a bridge structure as illustrated in FIGS. 7A to 7C as a gas sensor. While FIGS. 7A to 7C illustrate the configuration of a gas sensor schematically for simplicity and clarity of illustration, the size, thickness, and the like of the respective units are not drawn to scale. The bridge structure has high thermal insulating properties and low thermal capacity similarly to the diaphragm structure and can be employed as a gas sensor. The gas sensor 10' includes a Si substrate 1, a thermal insulation supporting layer 2, a heater layer 3, an electric insulation layer 4, a gas detecting unit 5, a through-hole 6, and a cavity 7. The Si substrate 1, the thermal insulation supporting layer 2, the heater layer 3, the electric insulation layer 4, and the gas detecting unit 5 have the same configuration as that of the gas sensor 10 described with reference to FIG. 2, and will be denoted by the same reference numerals, and redundant description thereof will not be provided.

In the gas sensor 10', the Si substrate 1, the thermal insulation supporting layer 2, the heater layer 3, the electric insulation layer 4, and the gas detecting unit 5 are formed in the above-described manner. After that, wet-etching is performed from the upper side so that four bridges and a central stage remain to form the cavity 7 having a quadrangular pyramid shape or a truncated quadrangular pyramid shape (not illustrated) as illustrated in FIGS. 7B and 7C which are sectional views along line A-A and B-B, respectively. Heater may be driven according to the above-described manner in the gas sensor 10' to form a gas detecting device that detects gases having a concentration as low as ppb levels.

Example 1

Subsequently, the characteristics of the gas detecting device and the gas detection method according to the present disclosure were examined while changing the driving conditions. The characteristics are illustrated in Table 1.

TABLE 1

| | Driving Conditions | | | | |
|---|---|---|---|---|---|
| | $T_0 = T_2 = T_3$ | $T_1$ | $t_0 = t_2 = t_3$ | $t_1$ | Gas Sensitivity |
| Example A | 220° C. | 20° C. | 0.6 s | 20 s | 77.2 |
| Example B | 270° C. | 20° C. | 0.6 s | 20 s | 112.5 |
| Example C | 430° C. | 20° C. | 0.6 s | 20 s | 78.0 |
| Example D | 320° C. | 20° C. | 0.1 s | 20 s | 41.3 |
| Example E | 320° C. | 20° C. | 0.2 s | 20 s | 79.7 |
| Example F | 320° C. | 20° C. | 0.6 s | 20 s | 134.0 |
| Example G | 320° C. | 20° C. | 0.6 s | 10 s | 66.0 |
| Example H | 320° C. | 20° C. | 0.6 s | 5 s | 22.8 |
| Comparative Example A | 270° C. | — | — | — | 1.0 |
| Comparative Example B | 320° C. | — | — | — | 1.0 |

Figure 8:
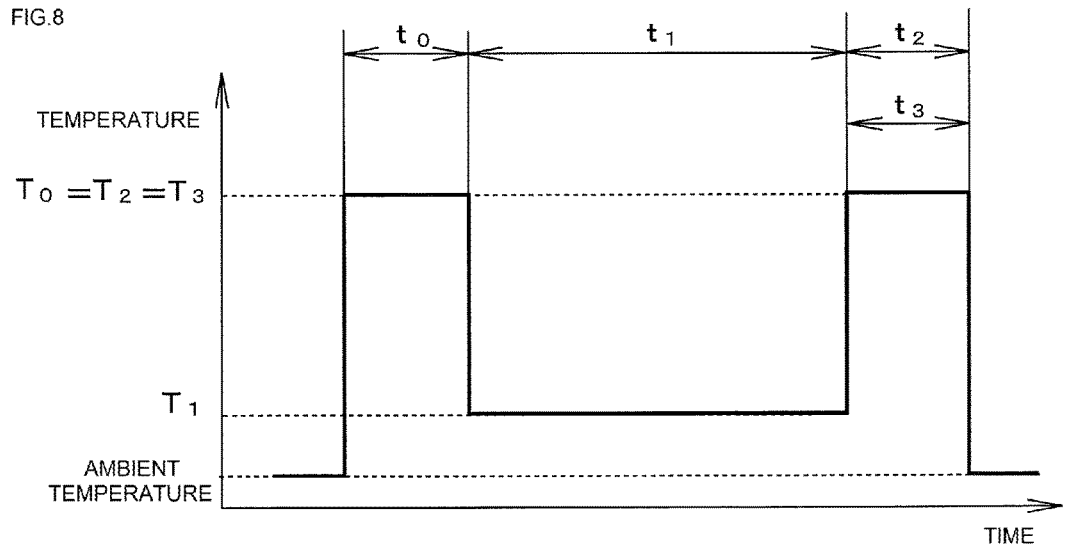
FIG. 8 is a driving pattern diagram for describing a heater layer driving scheme in Table 1.

Moreover, FIG. 8 illustrates a driving pattern diagram for describing a heater layer driving scheme illustrated in Table 1. In the case of Examples A to H, the target gas desorption step and the target gas detection step were performed in parallel as described above and were examined for comparison using the pattern of $T_1 < T_2 \leq T_0$. A material which is desorbed and detected in parallel was used for the material of the adsorption layer 5d and the gas sensing layer 5c.

In Examples A to H, the conditions of the oxygen adsorption temperature $T_0$, the target gas adsorption temperature $T_1$, the target gas desorption temperature $T_2$, and the target gas detection temperature $T_3$ in the gas detecting device 100 illustrated in FIGS. 1 and 2 were changed. In Comparative Examples A and B, the gas detecting device illustrated in FIGS. 1 and 2 was used, and the heater was driven at a constant temperature only.

The gas detecting devices of Examples A to H and Comparative Examples A and B had a gas sensitivity of 8-ppm ethanol. In these examples, sensitivities were evaluated under the conditions of $T_0=T_2=T_3$ and $T_1$=ambient temperature by repeating the pattern of FIG. 8 periodically so that the resistance of the gas sensing layer 5c was stabilized sufficiently. Moreover, the sensitivity was calculated by $R_{air}/R_{gas}$ which is the ratio of $R_{air}$ (resistance in clean air) to $R_{gas}$ (resistance in gas). Thus, the gas sensitivity of 1.0 means that there is no change in the sensor resistance (that is, the gas detecting device is not sensitive to gases).

The gas detecting devices of Comparative Examples A and B are not sensitive to gases. This may result from the fact that oxygen adsorption does not occur. The gas detecting devices of Examples A to H are sensitive to gases.

The influence of respective parameters was examined for respective examples. In Examples A, B, C, and F, the influence of changing the oxygen adsorption temperature $T_0$, the target gas desorption temperature $T_2$, and the target gas detection temperature $T_3$ was examined. In Example F, although the sensitivity was maximized when the oxygen adsorption temperature $T_0$, the target gas desorption temperature $T_2$, and the target gas detection temperature $T_3$ were 320° C., it is considered that this sensitivity is determined by chemical reaction of ethanol.

In Examples D, E, and F, the influence of the oxygen adsorption period $t_0$, the target gas desorption period $t_2$, and the target gas detection period $t_3$ was examined. In Example F, the sensitivity reaches its maximum when the oxygen adsorption period $t_0$, the target gas desorption period $t_2$, and the target gas detection period $t_3$ were 0.6 s. It is considered that the sensitivity increases as the period increases, and during this period, a reaction progresses in the direction of increasing the sensitivity.

In Examples F, G, and H, the influence of the target gas adsorption period $t_1$ was examined. The sensitivity increases as the target gas adsorption period $t_1$ increases, and the sensitivity for Example F was the largest. It is considered that adsorption-based condensation requires a certain period.

Figure 9:
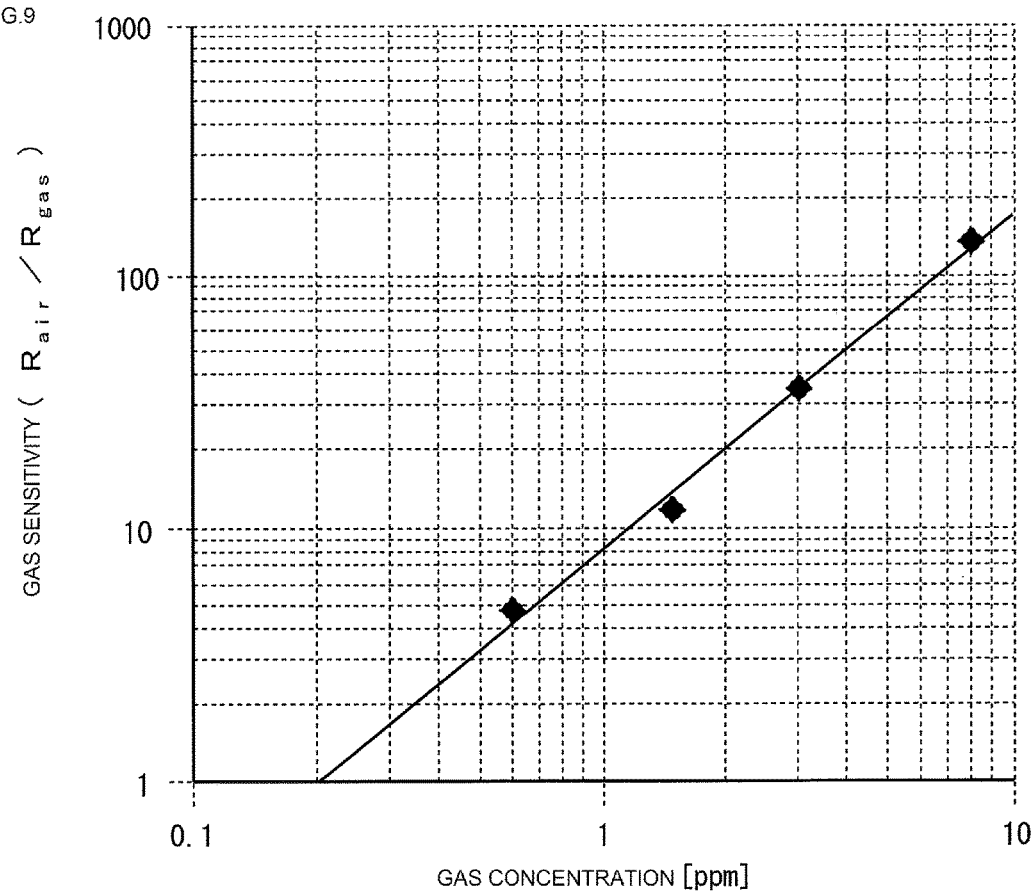
FIG. 9 is a characteristic diagram illustrating an ethanol concentration dependence of a gas sensitivity.

FIG. 9 illustrates the evaluation results of ethanol sensitivity in a lower concentration region under the conditions of Example F which provided highest sensitivity. It can be understood that linear sensitivity is obtained up to several hundreds of ppb levels.

Example 2

Next, experiments were conducted to verify whether the gas detecting device of the present disclosure is actually sensitive to a low-concentration target gas. The sensitivity was verified for ethanol, acetone, and isoprene which is VOC as a target gas. A sample gas that contains one of ethanol, acetone, and isoprene in low concentration (1 ppm or lower) was generated, and the sensitivity of the gas detecting device for this sample gas was examined. In this case, the best condition was examined while changing the driving conditions.

Figure 10:
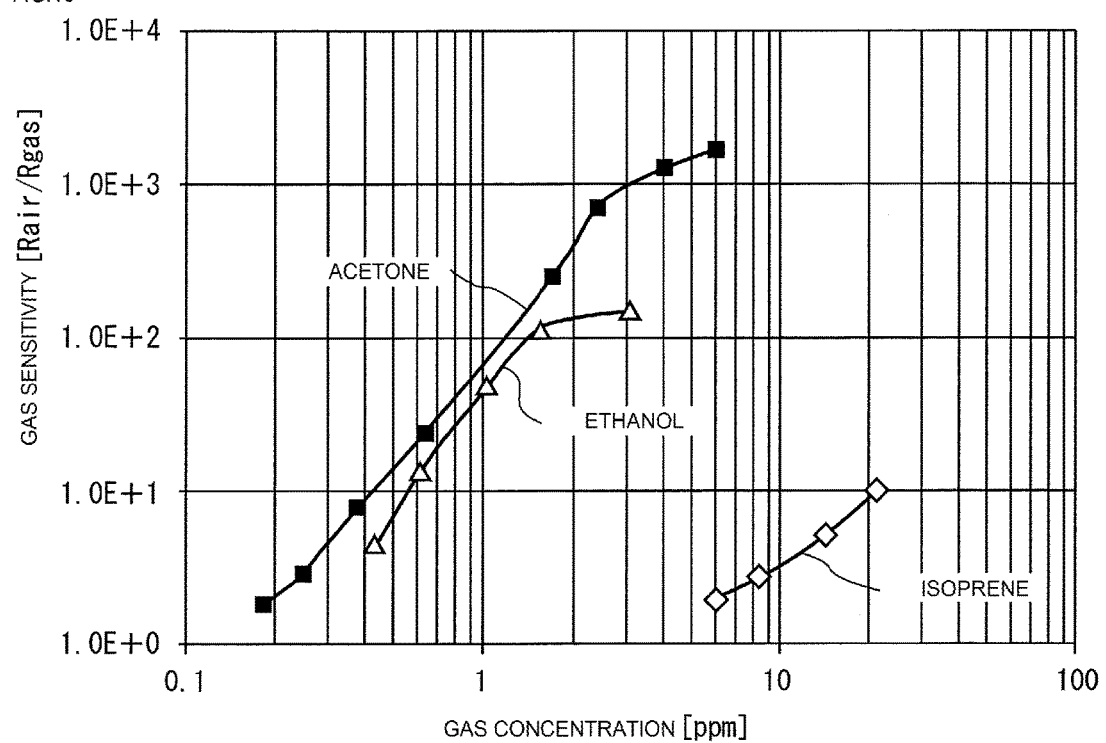
FIG. 10 is a gas concentration-gas sensitivity characteristic diagram of a gas detecting device.

When the target gas was acetone, highest sensitivity was obtained under a driving condition that the target gas adsorption period $t_1$ was 30 s, the target gas desorption period $t_2$ was 700 ms, and the heater voltage for realizing the target gas desorption temperature was 1.45 V. It was verified from an experiment that the target gas was detected in concentration as low as 1 ppm or lower, as illustrated in FIG. 10.

When the target gas was ethanol, highest sensitivity was obtained under a driving condition that the target gas adsorption period $t_1$ was 20 s, the target gas desorption period $t_2$ was 400 ms, and the heater voltage for realizing the target gas desorption temperature was 1.48 V. It was verified from an experiment that the target gas was detected in concentration as low as 1 ppm or lower, as illustrated in FIG. 10.

When the target gas was isoprene, highest sensitivity was obtained under a driving condition that the target gas adsorption period $t_1$ was 20 s, the target gas desorption period $t_2$ was 500 ms, and the heater voltage for realizing the target gas desorption temperature was 1.43 V. It was verified from an experiment that the target gas was not detected in concentration as low as 1 ppm or lower, as illustrated in FIG. 10.

As discussed above, it was confirmed from the gas sensitivity characteristics that a sensitivity of ppb levels which is the target of the present disclosure was obtained in a low concentration range of 1 ppm or lower for ethanol and acetone. However, the sensitivity was low for isoprene.

Figure 11:
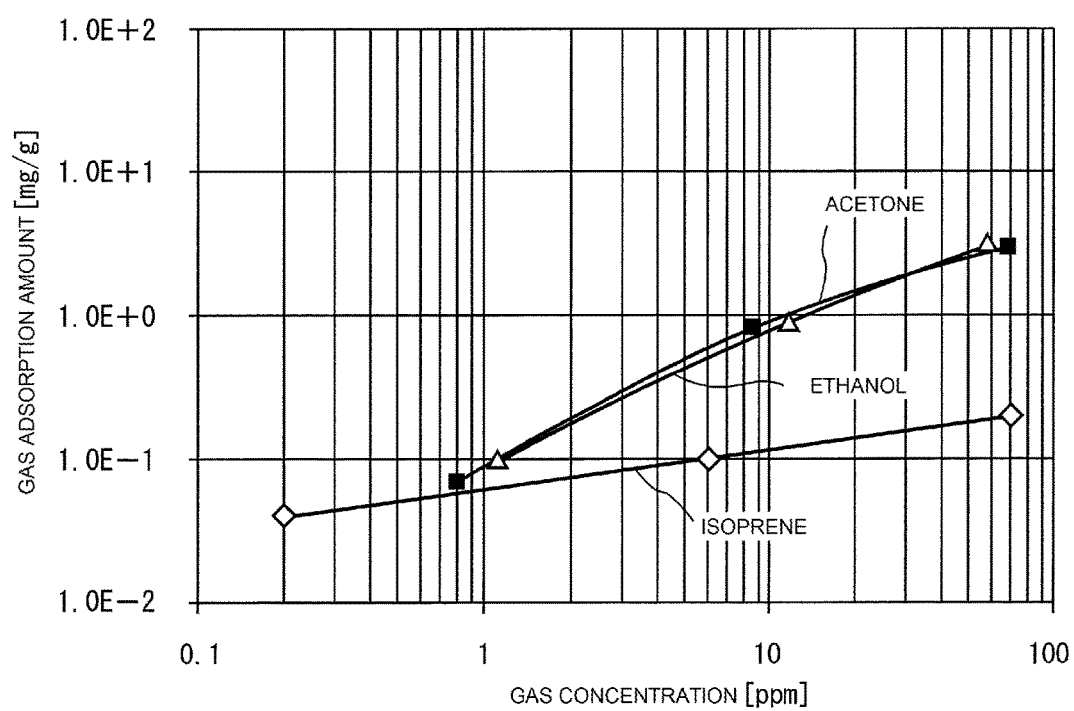
FIG. 11 is a gas concentration-gas adsorption amount characteristic diagram of a gas detecting device.

Such sensitivity is considered to be proportional to the adsorption amount of the target gas (VOC) condensed to the adsorption layer 5d. In order to verify this consideration, the amount of VOC adsorbed to the adsorption layer 5d which is a porous catalyst and temperature-programmed desorption of VOC were analyzed. The adsorption amount analysis results are illustrated in FIG. 11. From FIG. 11, it was found that the adsorption amount was approximately the same for ethanol and acetone and was small for isoprene. This adsorption amount profile is identical to the sensitivity profile and supports the high-sensitivity model discussed above.

Hereinabove, the gas detecting device and the gas detection method according to the present disclosure has been described.

According to the present disclosure, the heater layer 3 is driven according to a heater driving pattern that makes the most of the temperature characteristics of the gas sensing layer 5 of the gas sensor 10 having the structure illustrated in FIG. 2 and FIGS. 7A to 7C so that the target gas is adsorbed to the adsorption layer 5d in high concentration and reacts with the gas sensing layer 5c ($SnO_2$ layer). Thus, it is possible to detect a low-concentration target gas.

The gas detecting device and the gas detection method according to the present invention can detect gases having a concentration as low as ppb levels, and can be ideally useful in an environmental field for analyzing an indoor environment for the purpose of preventing a sick house syndrome and a medical field for analyzing the breath that a person exhales for the purpose of managing health conditions.

In embodiments according to the present disclosure, including those discussed above, functionalities (including those relating to control, calculation, computing and/or processing) of the drive processing unit may be implemented in the form of at least one hardware processor configured to carry out these functionalities. That is, the performance of any one or more of the functionalities may be accomplished by a single hardware processor, or be divided, in any manner known to those skilled in the art, among multiple hardware processors.

Reference signs and numerals are as follows:
100: Gas detecting device
10, 10': Gas sensor 1: Si substrate
2: Insulation supporting layer
2a: Thermal oxide SiO$_2$ layer
2b: CVD-Si$_3$N$_4$ layer
2c: CVD-SiO$_2$ layer
3: Heater layer
4: Electric insulation layer
5: Gas detecting unit
5a: Bonding layer
5b: Sensing layer electrode
5c: Sensing layer (SnO$_2$ layer)
5d: Adsorption layer (PdO supporting Al$_2$O$_3$ sintered material)
6: Through-hole
7: Cavity
20: Drive processing unit Although a few embodiments have been shown and described, it would be appreciated by those skilled in the art that changes may be made in these embodiments without departing from the principles and spirit of the invention, the scope of which is defined in the claims and their equivalents.

What is claimed is:

1. A gas detecting device comprising:
   a gas detecting unit having
     a gas sensing layer, and
     an adsorption layer;
   a heater layer configured to heat the gas detecting unit; and
   a drive processing unit configured to supply current to drive the heater layer and to acquire a sensor resistance from the gas sensing layer, the drive processing unit comprising at least one hardware processor configured to
     drive the heater layer for an oxygen adsorption period $t_0$ at an oxygen adsorption temperature $T_0$ at which oxygen is adsorbed to the gas sensing layer,
     after the oxygen adsorption period $t_0$ has elapsed, drive the heater layer for a target gas adsorption period $t_1$ at a target gas adsorption temperature $T_1$ at which a target gas adsorbs to the adsorption layer, such that in the target gas adsorption period a concentration of the target gas adsorbed to the adsorption layer increases so as to reach an equilibrium condition and a lame amount of oxygen is not desorbed from the gas sensing layer,
     after the target gas adsorption period $t_1$ has elapsed, drive the heater layer for a target gas desorption period $t_2$ at a target gas desorption temperature $T_2$ at which the target gas adsorbed to the adsorption layer is desorbed from the adsorption layer, such that in the target gas desorption period $t_2$, the target gas moves from the adsorption layer to the gas sensing layer to thereby react with oxygen in the gas sensing layer, and
     calculate a gas concentration of the target gas from a value of the sensor resistance of the gas sensing layer after the target gas desorption period $t_2$ has elapsed.

2. The gas detecting device according to claim 1, wherein the target gas adsorption period $t_1$ is longer than the oxygen adsorption period $t_0$ and is longer than the target gas desorption period $t_2$.

3. The gas detecting device according to claim 2, wherein the oxygen adsorption temperature $T_0$, the target gas adsorption temperature $T_1$, and the target gas desorption temperature $T_2$ satisfy a relation of $T_1<T_2 \leq T_0$.

4. The gas detecting device according to claim 1, wherein the oxygen adsorption temperature $T_0$, the target gas adsorption temperature $T_1$, and the target gas desorption temperature $T_2$ satisfy a relation of $T_1<T_2 \leq T_0$.

5. The gas detecting device according to claim 1, wherein the at least one hardware processor is further configured to drive the heater layer for a target gas detection period $t_3$ at a target gas detection temperature $T_3$ at which the target gas is detected in the gas sensing layer after the target gas desorption period $t_2$ has elapsed, and to calculate the gas concentration of the target gas from the sensor resistance of the gas sensing layer in the target gas detection period $t_3$.

6. The gas detecting device according to claim 5, wherein the target gas adsorption period $t_1$ is longer than the oxygen adsorption period $t_0$, is longer than the target gas desorption period $t_2$, and is longer than the target gas detection period $t_3$.

7. The gas detecting device according to claim 6, wherein the oxygen adsorption temperature $T_0$, the target gas adsorption temperature $T_1$, the target gas desorption temperature $T_2$, and the target gas detection temperature $T_3$ satisfy a relation of $T_1<T_3 \leq T_2 \leq T_0$ or $T_1<T_2 \leq T_3 \leq T_0$.

8. The gas detecting device according to claim 5, wherein the oxygen adsorption temperature $T_0$, the target gas adsorption temperature $T_1$, the target gas desorption temperature $T_2$, and the target gas detection temperature $T_3$ satisfy a relation of $T_1<T_3 \leq T_2 \leq T_0$ or $T_1<T_2 \leq T_3 \leq T_0$.

9. The gas detecting device according to claim 1, further comprising:
   a silicon substrate having a through-hole or cavity under the gas detecting unit;
   a thermal insulation supporting layer disposed on the silicon substrate, covering over the through-hole or cavity, and comprising a SiO$_2$ layer; and
   a silicon oxide film on the thermal insulation supporting layer, in which the heater layer is disposed, and supporting the gas detecting unit thereon.

10. The gas detecting device according to claim 1, wherein, in the oxygen adsorption period $t_0$, oxygen is adsorbed to the gas sensing layer to saturation.

11. A gas detection method comprising:
   adsorbing oxygen to a gas sensing layer by heating a gas detecting unit, which includes the gas sensing layer and an adsorption layer, for an oxygen adsorption period $t_0$ at an oxygen adsorption temperature $T_0$ at which oxygen adsorbs to the gas sensing layer;
   after the oxygen adsorption period $t_0$ has elapsed, adsorbing a target gas to the adsorption layer by heating the gas detecting unit for a target gas adsorption period $t_1$ at a target gas adsorption temperature $T_1$ at which the target gas adsorbs to the adsorption layer, such that in the target gas adsorption period a concentration of the target gas adsorbed to the adsorption layer increases so as to reach an equilibrium condition and a large amount of oxygen is not desorbed from the gas sensing layer;
   after the target gas adsorption period $t_1$ has elapsed, desorbing the target gas absorbed to the adsorption later to move to the gas sensing layer by heating the gas detecting unit for a target gas desorption period $t_2$ at a target gas desorption temperature $T_2$ at which the target gas adsorbed to the adsorption layer is desorbed from the adsorption layer, such that in the target gas desorption period $t_2$, the target gas moves from the adsorption layer to the gas sensing layer to thereby react with oxygen in the gas sensing layer; and calculating a gas concentration of the target gas from a value of a sensor resistance of the gas sensing layer, after the target gas desorption period $t_2$ has elapsed.

12. The gas detection method according to claim 11, wherein the target gas adsorption period $t_1$ is longer than the oxygen adsorption period $t_0$ and is longer than the target gas desorption period $t_2$.

13. The gas detection method according to claim 12, wherein the oxygen adsorption temperature $T_0$, the target gas adsorption temperature $T_1$, and the target gas desorption temperature $T_2$ are in a relation of $T_1 < T_2 \leq T_0$.

14. The gas detection method according to claim 12, wherein calculating the gas concentration involves heating the gas detector for a target gas detection period $t_3$ at a target gas detection temperature $T_3$ at which the target gas is detected in the gas sensing layer after the elapse of the target gas desorption period $t_2$, and calculating the gas concentration of the target gas from the sensor resistance of the gas sensing layer in the target gas detection period $t_3$.

15. The gas detection method according to claim 14, wherein the oxygen adsorption temperature $T_0$, the target gas adsorption temperature $T_1$, the target gas desorption temperature $T_2$, and the target gas detection temperature $T_3$ are in a relation of $T_1 < T_3 \leq T_2 \leq T_0$ or $T_1 < T_2 \leq T_3 \leq T_0$.

16. The gas detection method according to claim 11, wherein the oxygen adsorption temperature $T_0$, the target gas adsorption temperature $T_1$, and the target gas desorption temperature $T_2$ satisfy a relation of $T_1 < T_2 \leq T_0$.

17. The gas detection method according to claim 11, wherein calculating the gas concentration involves heating the gas detecting unit for a target gas detection period $t_3$ at a target gas detection temperature $T_3$ at which the target gas is detected in the gas sensing layer after the elapse of the target gas desorption period $t_2$, and calculating the gas concentration of the target gas from the sensor resistance of the gas sensing layer in the target gas detection period $t_3$.

18. The gas detection method according to claim 17, wherein the target gas adsorption period $t_1$ is longer than the oxygen adsorption period $t_0$, is longer than the target gas desorption period $t_2$, and is longer than the target gas detection period $t_3$.

19. The gas detection method according to claim 17, wherein the oxygen adsorption temperature $T_0$, the target gas adsorption temperature $T_1$, the target gas desorption temperature $T_2$, and the target gas detection temperature $T_3$ are in a relation of $T_1 < T_3 \leq T_2 \leq T_0$ or $T_1 < T_2 \leq T_3 \leq T_0$.

20. The gas detection method according to claim 11, wherein in the oxygen adsorption period $t_0$, oxygen is adsorbed to the gas sensing layer to saturation.

* * * * *

UNITED STATES PATENT AND TRADEMARK OFFICE
CERTIFICATE OF CORRECTION

Page 1 of 1

PATENT NO. : 9,945,803 B2
APPLICATION NO. : 14/959634
DATED : April 17, 2018
INVENTOR(S) : Takuya Suzuki It is certified that error appears in the above-identified patent and that said Letters Patent is hereby corrected as shown below:

In the Claims

Column 15, Line 43:
In Claim 1, after "period" insert -- $t_1$, --.

Column 15, Line 46:
In Claim 1, delete "lame" and insert -- large --, therefore.

Column 16, Line 56:
In Claim 11, after "period" insert -- $t_1$, --.

Signed and Sealed this
Seventh Day of August, 2018

Andrei Iancu
*Director of the United States Patent and Trademark Office*